(12) United States Patent
Henderson

(10) Patent No.: US 8,623,035 B1
(45) Date of Patent: Jan. 7, 2014

(54) METHODS FOR RESECTION OF A LUMINAL STRUCTURE

(75) Inventor: Eric R. Henderson, Tampa, FL (US)

(73) Assignee: University of South Florida, Tampa, FL (US)

( * ) Notice: Subject to any disclaimer, the term of this patent is extended or adjusted under 35 U.S.C. 154(b) by 1273 days.

(21) Appl. No.: 12/117,390

(22) Filed: May 8, 2008

Related U.S. Application Data

(60) Provisional application No. 60/916,899, filed on May 9, 2007.

(51) Int. Cl.
*A61B 17/11* (2006.01)

(52) U.S. Cl.
USPC .......................................................... 606/153

(58) Field of Classification Search
USPC ......... 606/153, 115, 110, 149, 139, 142, 143, 606/170, 213, 215, 219–221; 227/175.1–182.1; 623/23.64, 23.65
See application file for complete search history.

(56) References Cited

U.S. PATENT DOCUMENTS

| | | | | |
|---|---|---|---|---|
| 3,193,165 A | * | 7/1965 | Burtsev et al. | 227/8 |
| 4,476,863 A | * | 10/1984 | Kanshin et al. | 606/153 |
| 4,592,354 A | * | 6/1986 | Rothfuss | 227/179.1 |
| 4,606,343 A | * | 8/1986 | Conta et al. | 227/178.1 |
| 4,703,887 A | * | 11/1987 | Clanton et al. | 227/19 |
| 4,893,622 A | * | 1/1990 | Green et al. | 227/180.1 |
| 4,907,591 A | * | 3/1990 | Vasconcellos et al. | 606/154 |
| 4,957,499 A | * | 9/1990 | Lipatov et al. | 606/153 |
| 5,261,920 A | * | 11/1993 | Main et al. | 606/153 |
| 5,309,927 A | * | 5/1994 | Welch | 128/898 |
| 5,669,918 A | * | 9/1997 | Balazs et al. | 606/139 |
| 6,117,148 A | * | 9/2000 | Ravo et al. | 606/153 |
| 6,736,822 B2 | | 5/2004 | McClellan et al. | |
| 7,074,220 B2 | * | 7/2006 | Hill et al. | 606/45 |
| 7,141,055 B2 | * | 11/2006 | Abrams et al. | 606/115 |
| 7,220,237 B2 | | 5/2007 | Gannoe et al. | |
| 7,285,125 B2 | | 10/2007 | Viola | |
| 7,338,505 B2 | | 3/2008 | Belson | |

(Continued)

OTHER PUBLICATIONS

D. W. Larson, E. Dozois, W. J. Sandborn and R. Cima. "Total laparoscopic proctocolectomy with Brooke ileostomy: a novel incisionless surgical treatment for patients with ulcerative colitis." Surgical Endoscopy. vol. 19. No 9. Sep. 2005. pp. 1284-1287.

(Continued)

*Primary Examiner* — Corrine M McDermott
*Assistant Examiner* — Christopher L Templeton
(74) *Attorney, Agent, or Firm* — Michele L. Lawson; Smith & Hopen, P.A.

(57) ABSTRACT

Provided is a method of resecting a luminal structure, such as a colon. A first luminal structure and a second luminal structure are defined by severing the original luminal structure. The second luminal structure is secured to the distal end of an elongate body disposed within the second luminal structure. Refraction of the elongate body forms a circumferential fold in the second luminal structure and isolates a tissue mass between the circumferential fold and the distal end of the elongate body. The second luminal structure is then transected circumferentially at or adjacent the circumferential fold, thus severing the tissue mass. The tissue mass is then removed by retracting the distal end of the elongate body. The free end of the second luminal structure is approximated with the free end of the first luminal structure and secured by conventional surgical methods. Instrumentation for use with the inventive method is also provided.

10 Claims, 10 Drawing Sheets

(56) References Cited

U.S. PATENT DOCUMENTS

| | | | |
|---|---|---|---|
| 2004/0092960 A1* | 5/2004 | Abrams et al. | 606/139 |
| 2006/0135992 A1* | 6/2006 | Bettuchi et al. | 606/219 |
| 2007/0038248 A1* | 2/2007 | Heinrch | 606/219 |

OTHER PUBLICATIONS

Leroy, J.; Jamali, F.; Forbes, L.; Smith, M.; Rubino, F.; Mutter, D.; Marescaux, J. "Laparoscopic total mesorectal excision (TME) for rectal cancer surgery: long-term outcomes." Surgical Endoscopy. vol. 18. No. 2. Feb. 2004. pp. 281-289.

Thibault, C, Poulin, E C. "Total laparoscopic proctocolectomy and laparoscopy-assisted proctocolectomy for inflammatory bowel disease: operative technique and preliminary report." Surg-Laparosc-Endosc. Dec. 1995 vol. 5. No. 6. pp. 472-476.

Reissman P, Salky BA, Pfeifer J, Edye M, Jagelman DG, Wexner SD. "Laparoscopic surgery in the management of inflammatory bowel disease." Am J Surg. Jan. 1996 vol. 171. No. 1 pp. 47-50.

Araki, Y., Matsumoto, A., Isomoto, H. "Total colectomy combined laparoscopy." Minimally Invasive Therapy and Allied Technologies. vol. 9. No. 1.2000. pp. 3-6.

Wexner SD, Moscovitz ID. "Laparoscopic colectomy in diverticular and Crohn's disease." Surg Clin North Am. Aug. 2000. vol. 80 No. 4. pp. 1299-1319.

Ludwig, K. A., Jerby, B. L. "Laparoscopic procedures in patients with Crohn's disease." Semin. Colon Rectal Surg. vol. 10. No. 2. 1999. pp. 85-93.

N. Pokala, C. P. Delaney, A. J. Senagore, K. M. Brady and V. W. Fazio. "Laparoscopic vs open total colectomy: a case-matched comparative study." Surgical Endoscopy. vol. 19. No. 4. Apr. 2005. pp. 531-535.

http://www.lapsurgery.com/colectom.htm, Accessed Jun. 16, 2008.

\* cited by examiner

METHODS FOR RESECTION OF A LUMINAL STRUCTURE

CROSS REFERENCE TO RELATED APPLICATIONS

This application claims priority to U.S. Provisional Application No. 60/916,899, filed May 9, 2007, which application is incorporated herein by reference.

BACKGROUND OF THE INVENTION

In 2001 an estimated 107,300 new cases of Colon Cancer were diagnosed and colon cancer resulted in 48,100 estimated deaths. Resection of the large intestine is a frequently performed operation most commonly used to treat colon cancer, the third most common cancer in both men and women in the U.S. at the time of this writing. Colectomy is also used in the treatment of conditions such as Crohn's disease, ulcerative colitis, and in cancer prevention in patients with conditions such as Familial Polyposis.

A move to less invasive surgeries has seen the advent of the laparoscopic-aided colectomy, in which the surgeon uses laparoscopic instruments to perform the bulk of the operation and finally, when the resected portion of colon is ready to be removed, an incision is made in the abdomen and the colon is removed. This operation spares the patient the large incisions that were required prior to the use of laparoscopic instruments, however, still necessitates a 12 cm incision for specimen removal.

SUMMARY OF INVENTION

Provided is a method of resecting a luminal structure, such as a colon, which obviates the need for large incisions. The instrumentation used with the inventive method removes the need to make an incision in order to remove the resected structure.

In the illustrative embodiment of a colon resection, the instrumentation disclosed herein addresses the need to make an incision in the abdomen in order to remove the resected colon. Rather than subject the patient to any incision other than the small, 1-2 cm, incisions required of the laparoscopic instruments, the invention includes instrumentation and associated methods that allow the resected colon to be removed through the anus. This method reduces duration of hospital stays by decreasing the trauma to the patient in the operating room. By avoiding a large incision the incidence of wound infections is lessened as is the incidence of incisional hernias and wound dehiscence, feared complications of large incisions.

In a first embodiment, the invention includes a method of resecting a portion of a luminal structure by defining a first luminal structure and a second luminal structure by severing the original luminal structure. The interior tissue of the second luminal structure is secured to the distal end of an elongate body disposed within the second luminal structure. Partial retraction of the distal end of the elongate body forms a circumferential fold in the second luminal structure and isolates a tissue mass between the circumferential fold and the distal end of the elongate body. The second luminal structure is then transected circumferentially at or adjacent the circumferential fold, thereby severing the tissue mass. The tissue mass is then removed by retracting the distal end of the elongate body. The free end of the second luminal structure is then urged against the free end of the first luminal structure and the two structures are secured by conventional surgical methods, such as with a surgical stapler.

In an alternate embodiment, the invention includes a method of resecting a portion of a luminal structure by inserting a device with 3 tissue fixing heads into a luminal structure past a desired point of resection. For ease of reference, the tissue fixing heads are referred to as the distal head, medial head and proximal head. The distal head is disposed on the distal end of a first elongate body. The medial head and proximal head are disposed on the distal end of a second elongate body that has a lumen running through its length. The second elongate body therefore slides over the first elongate body. The medial head is adjacent the distal head when the second elongate body is at its further extent over the first elongate body.

Once positioned, a first suture is tied around the outside of the luminal structure between the distal head and medial head such that the tissue of the luminal structure is held securely against the distal head or first elongate body. A second suture is similarly tied around the outside of the luminal structure between the medial head and proximal head. The luminal structure is then transected between the first and second sutures thereby defining a first luminal structure and a second luminal structure. The second elongate body is then partially retracted (over the first elongate body) causing the medial and proximal heads to move away from the distal head and the free end of the second luminal structure to fold in circumferentially on itself (invaginate).

A third suture is tied around the interior of the circumferential fold thereby isolating a tissue mass between the third suture the medial head. The tissue mass is then severed and withdrawn by retracting the second elongate body. The free end of the second luminal body (adjacent the third suture) is then urged into contact with the free end of the first luminal body (adjacent the first suture) by sliding a joining device over the first elongate body into operative communication with the distal head. The free ends are then secured to one another by known surgical methods, such as with a surgical stapler.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
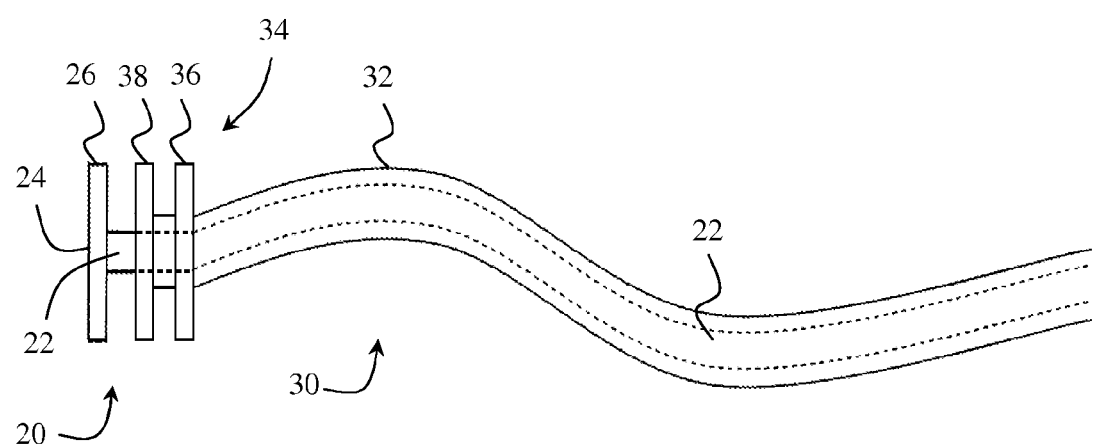
FIG. 1 is a side view of a surgical device for use with the current invention.

The invention, along with its multiple embodiments, is described here in detail with reference to FIGS. 1-9 wherein like reference numerals identify similar or identical structures. As used herein, and as is traditional, the term "distal" refers that structure, or that portion of a structure, which is farthest from the point of insertion to the luminal structure and/or the operator. The term "proximal," in keeping with its traditional meaning, refers that structure, or that portion of a structure, which is closest the point of insertion to the luminal structure and/or the operator. While the description of the invention relates to resection of a portion of the colon, other embodiments may be utilized including utility in other luminal structures. Therefore, structural changes may be made without departing from the scope of the invention.

Referring now to FIG. 1, colectomy device 10 comprises distal approximating device 20 and folding device 30. Distal approximating device 20 further comprises guide tube 22 having leading end 24 and distal head 26. Guide tube 22 is a semi-rigid, non-compressible (lengthwise) structure. Optionally, guide tube 22 is steerable device such as the steerable endoscope described in U.S. Pat. No. 6,468,203. In one embodiment, distal head 26 is an anvil adapted to cooperate with a surgical stapler. In an alternate embodiment, distal head 26 comprises an expandable member and/or a gripping mechanism for gripping the wall of the colon. The expandable member may be an inflatable balloon or a mechanically expandable mechanism, as is known in the art. The gripping mechanism may comprise a plurality of circumferentially located ports within which attachment points, e.g., needles, hooks, barbs, etc., may be retractably positioned about an exterior surface of the expandable member. Alternatively, the gripping mechanism may be a vacuum gripper through a plurality of circumferentially located ports around distal head 26 or other known gripping mechanism.

Folding device 30 further comprises elongate body 32 having a lumen there through (not shown) and fixing mechanism 34. Fixing mechanism 34 further comprises proximal head 36 and medial head 38. Folding device 30 is provided such that it is slidably moveable over guide tube 22. Proximal head 36 and medial head 38 can be static structures or can comprise an expandable mechanism as with distal head. Furthermore, proximal head 36 and medial head 38 can include a gripping mechanism, discussed above.

Figure 2:
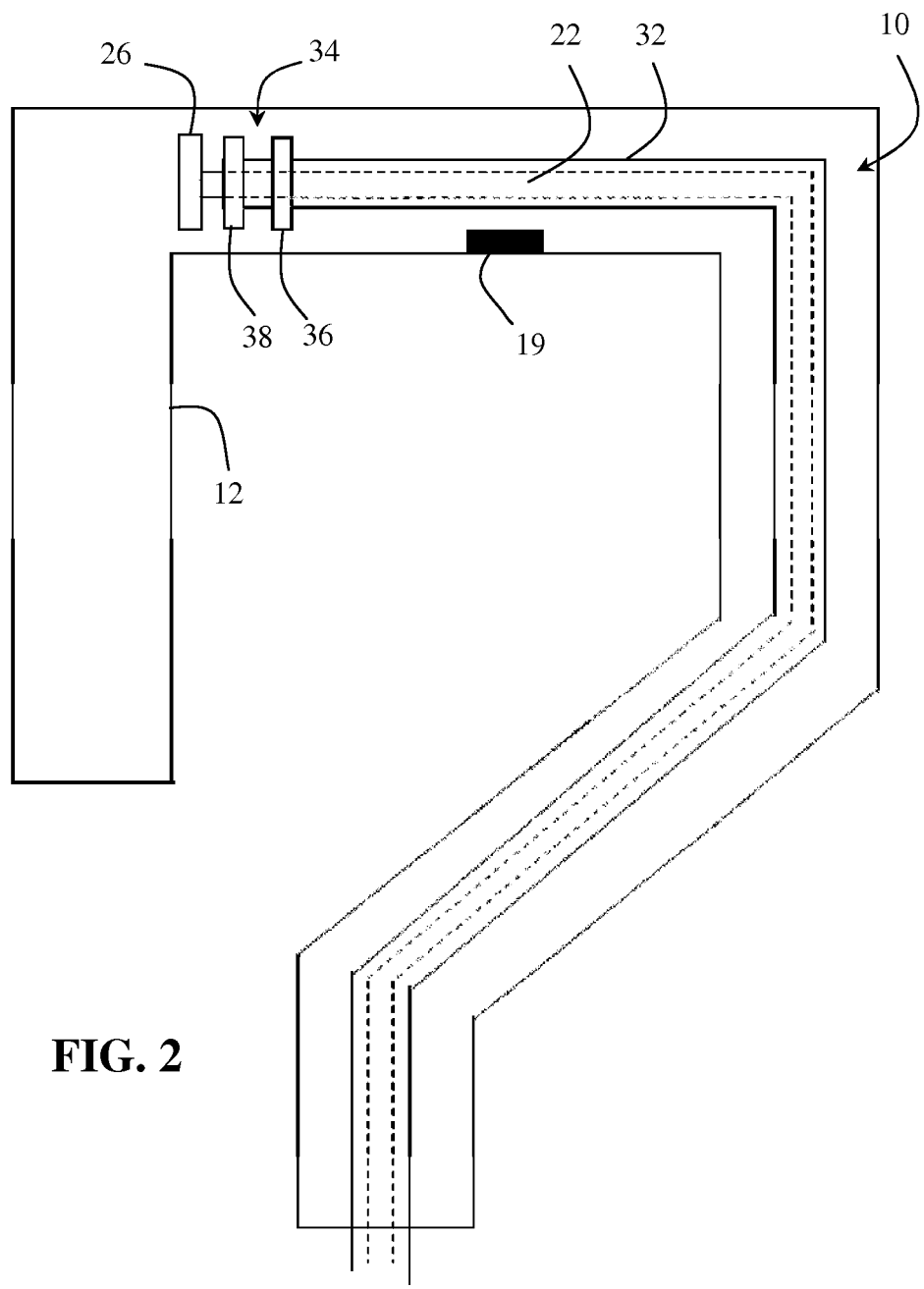
FIG. 2 is a block diagram showing the positioning of the surgical device of FIG. 1 within the luminal structure.

FIG. 2 is a cutaway drawing showing colectomy device 10 positioned within luminal structure 12, here a colon. In this example, distal head 26, medial head 38 and proximal head 36 are all positioned such that tumor (19) is proximal in relation to fixing mechanism 34. In other words, the diseased portion of colon is between the area of insertion (here the anus) and proximal head 36. The position of fixing mechanism 34 can be confirmed with an x-ray or with visualization with a colonoscope. The operator next inserts the laparoscopic instruments as usual and begins dissecting the colon's mesentery and ligating its blood supply. It is possible that the operator may find the added weight of colectomy device 10 in the colon slows progress. Optionally, colectomy device 10 can be inserted after the dissection.

Figure 3:
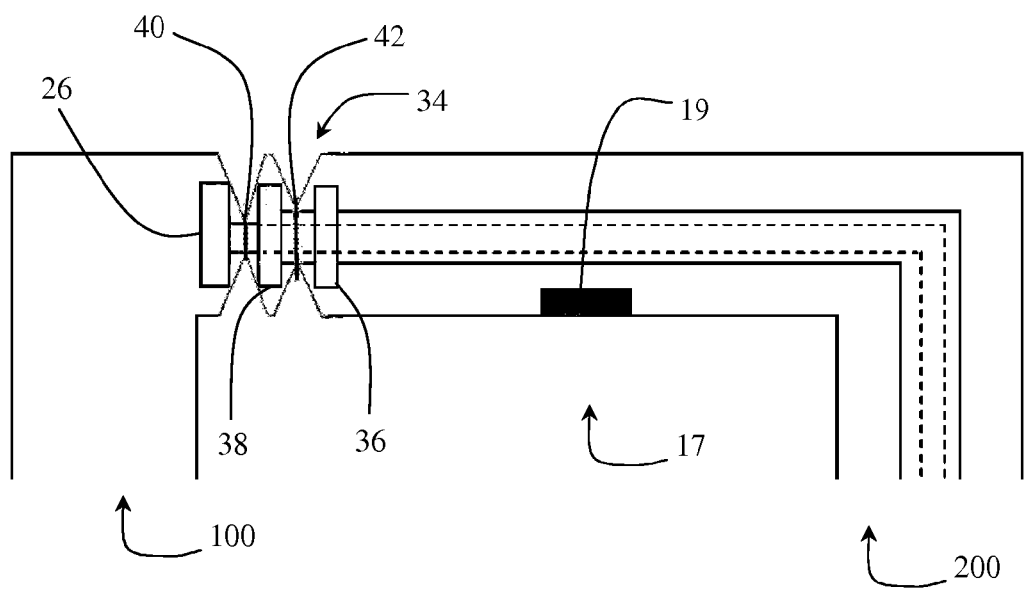
FIG. 3 is a block diagram showing how the luminal structure is secured to the surgical device of FIG. 1.

As seen in FIG. 3, when the section of colon to be removed (17) has been successfully mobilized (its blood supply cut off), first suture 40 is placed around the exterior of the colon wall adjacent the proximal side of distal head 26. Second suture 42 is similarly placed around the exterior of the colon wall between medial head 38 and proximal head 36. Following the placement of the sutures the colon would be cut between first suture 40 and second suture 42 thereby forming first luminal structure 100 and second luminal structure 200. First suture 40 and second suture 42 are placed with laparoscopic techniques.

Although this embodiment uses laparoscopically placed sutures, any method of circumferentially securing the luminal tissue firmly against guide tube 22 is contemplated. For example, distal head 26 can be a gripping mechanism (as discussed above), such as a vacuum, that applies sufficient gripping force to hold free end 105 of first luminal structure 100 tightly against guide tube 22 and/or the proximal surface of distal head 26. Similarly, fixing mechanism 34 can be adapted with a similar gripping mechanism sufficient to hold free end 205 of second luminal structure against elongate body 32 between proximal head 36 and medial head 38. Alternatively, fixing mechanism 34 can be adapted with a gripping mechanism sufficient to hold free end 205 of second luminal structure against either the proximal surface of medial head 38 and/or the distal surface of proximal head 36. The circumferentially secure attachment of the luminal wall to a surface of colectomy device 10, such as guide tube 22, prevents leakage of the contents of the colon into the peritoneal (i.e. abdominal) cavity.

Figure 4A:
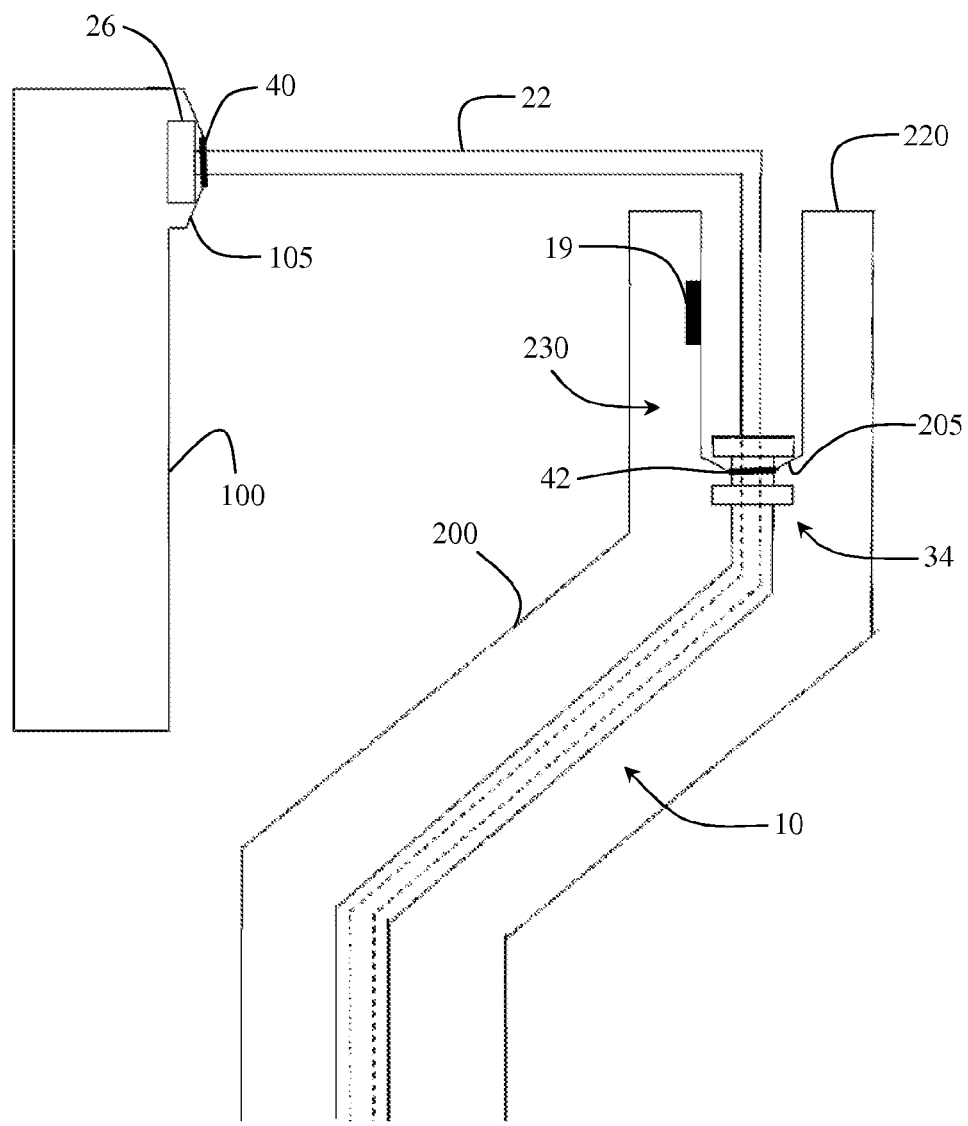
FIG. 4A is a block diagram showing one embodiment wherein the free end of the luminal structure is invaginated.
Figure 4B:
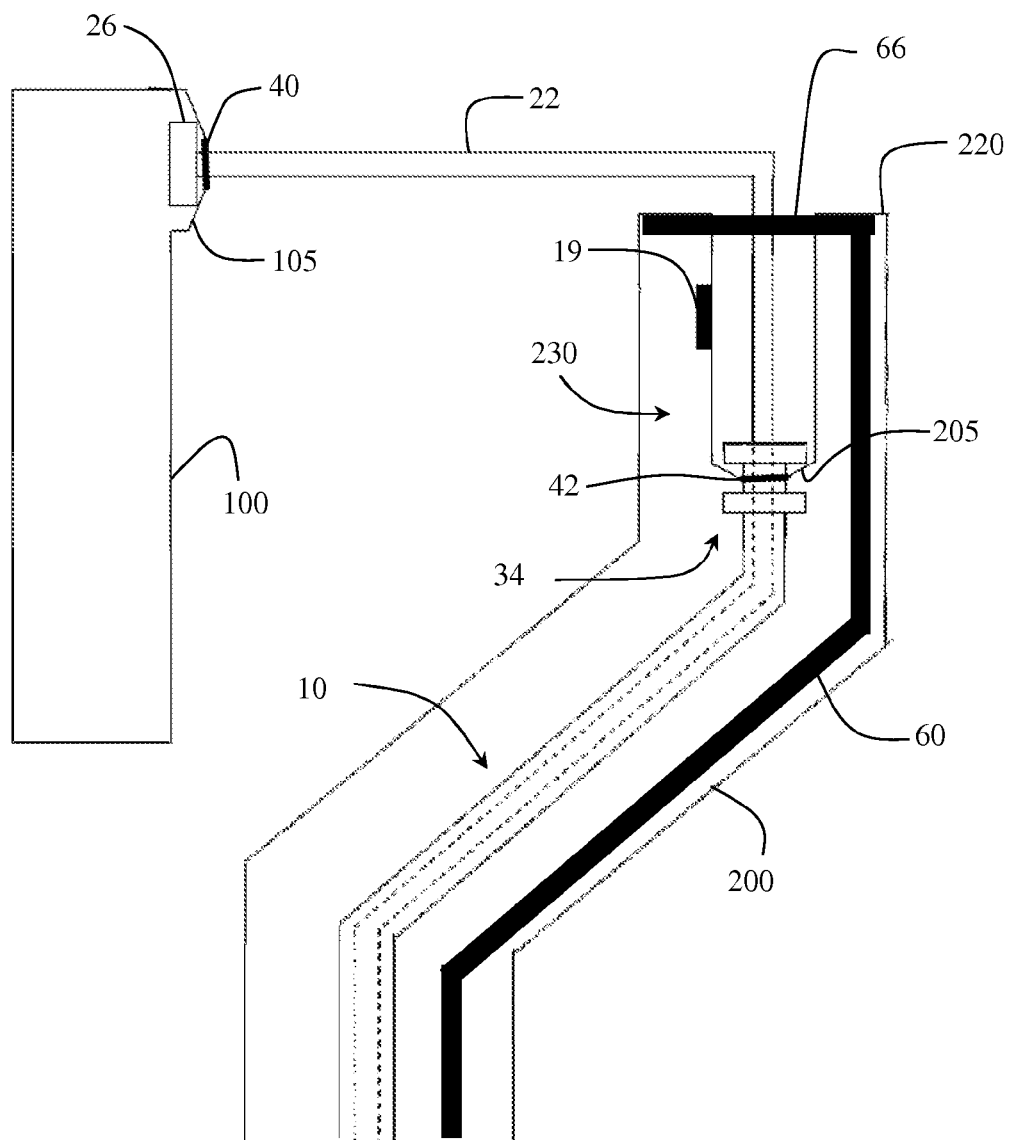
FIG. 4B is a block diagram showing an alternate embodiment wherein the free end of the luminal structure is invaginated.
Figure 5:
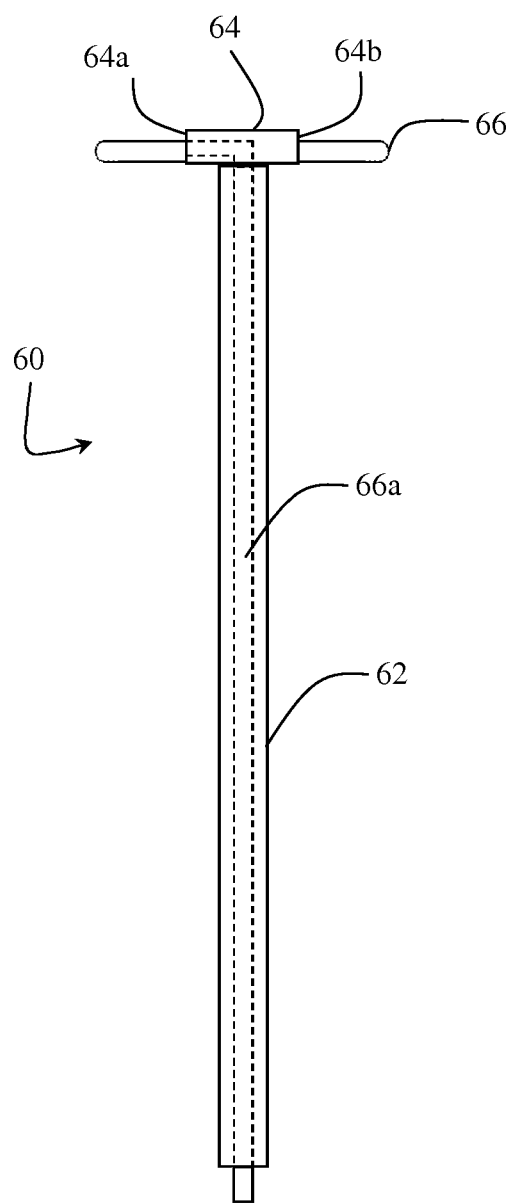
FIG. 5 is a side view of an alternate surgical device, the ring structure, for use with the current invention.
Figure 6:
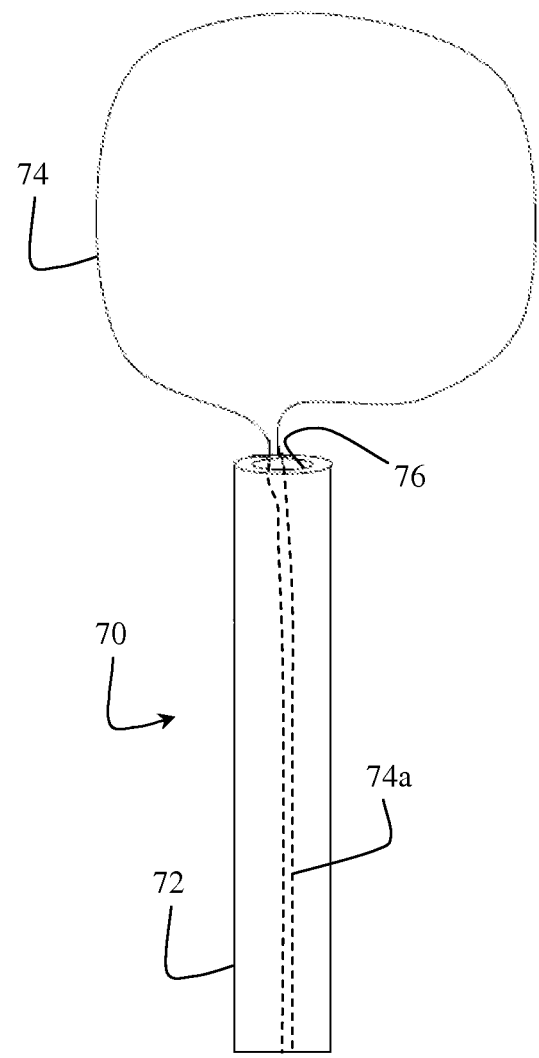
FIG. 6 is a side view of an alternate surgical device, the suturing device, for use with the current invention.

Free end 205 of second luminal structure 200 is then folded inward (invaginates) circumferentially to form a circumferential fold and a tissue mass (see FIGS. 4A and 4B). In a first embodiment, shown in FIG. 4A, a colonoscope (not shown) is inserted through the anus so that fixing mechanism 34 can be visualized. Air, or any suitable gas, is introduced into the second luminal structure causing it to radially expand. Fixing mechanism 34 is then slowly retracted, over guide tube 22, causing free end 205 of second luminal structure 200 to fold inward forming circumferential fold 220 and tissue mass 230. Tissue mass 230, generally, comprises the portion of tissue between circumferential fold 220 and second suture 42. The stopping point of retraction is where the mesentery (source of blood supply) is still attached to the colon (not shown). A colonoscope and/or laparoscope can be used to monitor the process.

An alternate embodiment, shown in FIG. 4B, utilizes a ring structure (FIG. 5) to assist in forming circumferential fold 220 and tissue mass 230. Ring structure 60 comprises outer tube 62, T-shaped head 64 and loop 66. Outer tube 62 is a hollow, semi-rigid tube with a lumen there through. Loop 66 is formed from semi-rigid, preferably solid, rod 66a which exits T-shaped head 64 on a first end 64a and then circles around to attach to the other side of the T-shaped head 64 on a second end 64b. The semi-rigid material of loop 66 is slidably disposed within the lumen of outer tube 62 to dilate loop 66.

Returning now to the alternate embodiment of FIG. 4B, a colonoscope (not shown) is inserted through the anus so that fixing mechanism 34 can be visualized. Air, or other suitable gas, is introduced into second luminal structure 200 causing it to radially expand. Ring structure 60 is then inserted longitudinally over colectomy device 10 until loop 66 is adjacent the interior of free end 205 of second luminal structure 200, and by extension fixing mechanism 34.

Once ring structure 60 is inserted to where loop 66 is around fixing mechanism 34, loop 66 is expanded radially by sliding rod 66a forward. Fixing mechanism 34 is then slowly retracted, over guide tube 22, causing free end 205 of second luminal structure 200 to fold inward forming circumferential fold 220 and tissue mass 230. Ring structure 60 is also retracted, however, but at about half the rate of fixing mechanism 34 as it is used to ensure the colon folds inward upon itself. A colonoscope and/or laparoscope can be used to monitor the process. The stopping point of retraction is where the mesentery (source of blood supply) is still attached to the colon (not shown). When the colon has been folded upon itself a sufficient amount, ring structure 60 is removed.

Figure 7:
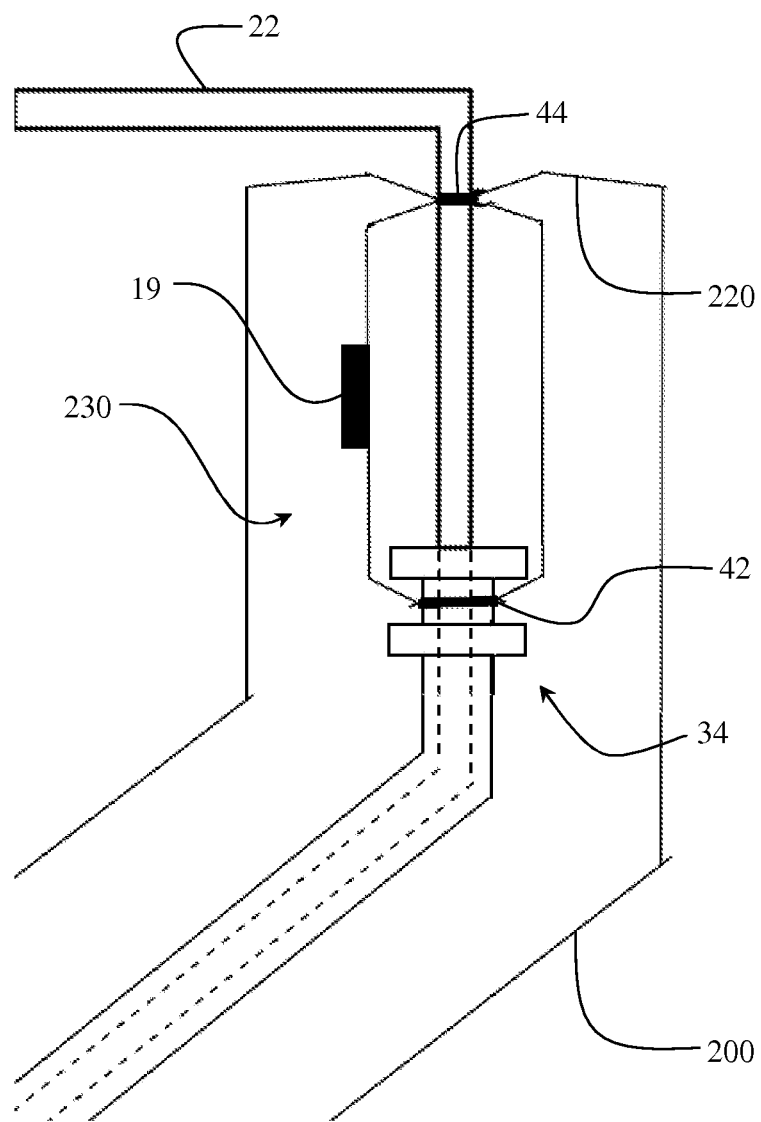
FIG. 7 is a block diagram showing how the circumferential fold is secured to the surgical device of FIG. 1.
Figure 8:
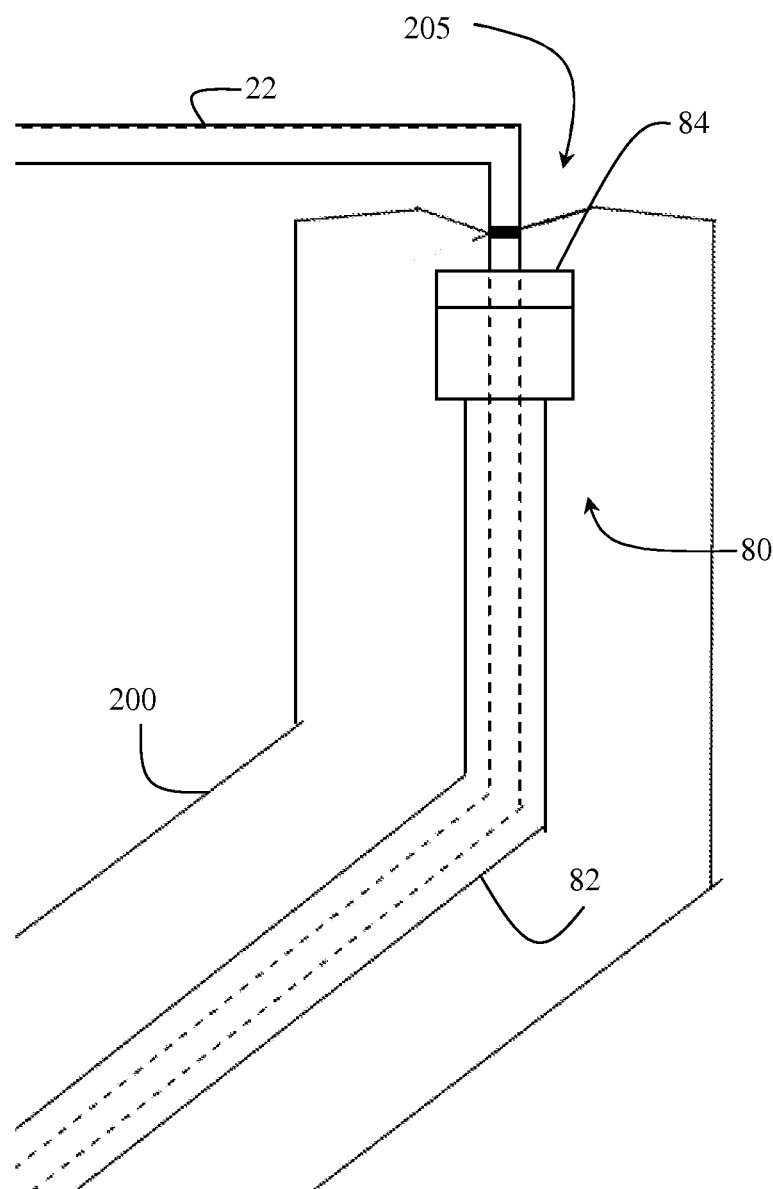
FIG. 8 is a block diagram showing the insertion and structure of an alternate surgical device, the tissue connecting device, for use with the current invention.

Once circumferential fold 220 and tissue mass 230 are properly defined, suturing device 70 (FIG. 6) is used to place third suture 44 on the inner surface circumferential fold 220. Third suture 44 firmly secures the tissue of circumferential fold 220 against guide tube 22 (FIG. 7). Suturing device 70 comprises semi-rigid rod 72 and suture loop 74. Suture material 74a is disposed through lumen 76 in rod 72. A locking device (not shown) allows suture material 74a to be pulled through lumen 76 to tighten suture loop 74 but does not allow the loop to loosen once tightened. The diameter of the locking device is less than the diameter of the inner diameter of rod 72 so that suture loop 74 is tightened when rod 72 is pushed inward and/or the suture material 74a is pulled proximally through lumen 76.

Suturing device 70 is inserted longitudinally with folding device 30 in the lumen formed by suture loop 74. Suture loop 74 passes over folding device 30 and past fixing mechanism 34 until it is adjacent the inner surface of circumferential fold 220. Rod 72 is then pushed forward, causing the locking device to cinch suture loop 74 against guide tube 22 (FIG. 7). An electric cautery knife on the colonoscope, or other cutting device, is then used to transect the colon wall proximally of circumferential fold 220 thereby severing tissue mass 230. Tissue mass 23, which is retained by fixing mechanism 34, is removed through the anus by retracting fixing mechanism 34.

Proximal approximating device 80 is then used to join free end 205 of second luminal structure 200 to free end 105 of first luminal structure 100. Proximal approximating device 80 (FIG. 8) comprises elongate body 82, which has a lumen there through, and joining mechanism 84 disposed on the distal end of elongate body 82. In one embodiment, joining mechanism 84 is a surgical stapling device similar to the transanal, circumferential staplers known in the art (i.e. PROXIMATE ILS™ and ENDOPATH STEALTH™ intraluminal staplers from Ethicon Endo-Surgery, Inc.). In this embodiment, joining mechanism 84 is a surgical stapler adapted to cooperate with an anvil disposed on distal head 26.

Figure 9:
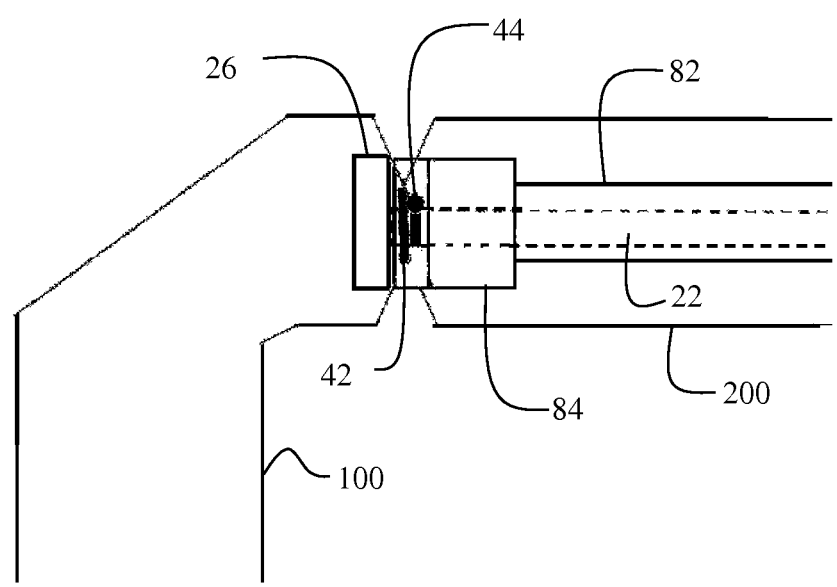
FIG. 9 is a block diagram showing the approximation of the free ends of the severed luminal structure as well as the cooperative communication between the tissue connecting device and the distal end of the surgical device of FIG. 1.

Proximal approximating device 80, as shown in FIG. 9, is inserted longitudinally over guide tube 22. Proximal approximating device 80 is slidably displaced over guide tube 22, and/or guide tube 22 is withdrawn through the lumen of proximal approximating device 80, until free end 205 of second luminal structure 200 and free end 105 of first luminal structure 100 are adjacent. Joining device 84 is then activated thereby affixing free end 205 of second luminal structure 200 to free end 105 of first luminal structure 100. The final result is the anastomosed colon as shown in FIG. 9.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of resecting a portion of a luminal structure, comprising:
    inserting a surgical device comprising a tissue approximation head, a first tissue resection head and a second tissue resection head into the luminal structure past a portion to be resected, wherein the tissue approximation head is disposed at a distal end of a first elongate body defining a longitudinal axis;
    circumferentially securing the luminal structure to the surgical device proximal to the tissue approximation head;
    circumferentially securing the luminal structure to the surgical device between the first tissue resection head and the second tissue resection head;
    severing the luminal structure between the tissue approximation head and the first tissue resection head to form a first luminal structure and a second luminal structure;
    inverting a severed end of the second luminal structure within the second luminal structure forming a circumferential fold, whereby the portion to be resected is between the circumferential fold and the first tissue resection head;
    securing the second luminal structure to the first elongate body distally of the first and second tissue resecting heads prior to severing the second luminal structure at or near the circumferential fold;
    severing the second luminal structure at or near the circumferential fold; and
    withdrawing the first and second tissue resection heads from the luminal structure inserting a tissue connection device into the second luminal structure adjacent a free end thereof; approximating the free end of the second luminal structure with a free end of the first luminal structure; and securing the free end of the second luminal structure with the free end of the first luminal structure.

2. The method of claim 1, wherein the luminal structure is secured to the surgical device with a fastener selected from the group consisting of staples, clips, screws, adhesives, sutures and combinations thereof.

3. The method of claim 1, wherein the severed end of the second luminal structure is inverted within the second luminal structure by partially retracting the first and second tissue resection heads away from the tissue approximation head.

4. The method of claim 1, wherein the luminal structure is secured circumferentially to the first elongate body proximal to the tissue approximation head.

5. The method of claim 1, wherein the first and second tissue resection heads are disposed near the distal end of a second elongate body, having a lumen adapted to receive the first elongate body, defining a longitudinal axis.

6. The method of claim 5, wherein the luminal structure is circumferentially secured to the second elongate body between the first tissue resection head and the second tissue resection head.

7. The method of claim 1, wherein the first tissue resection head and the second tissue resection head are adapted to slide longitudinally relative to the tissue approximation head along at least a portion of the first elongate body.

8. The method of claim 1, wherein:
    the tissue connection device is disposed near the distal end of a third elongate body, having a lumen adapted to receive the first elongate body.

9. The method of claim 8, wherein the free end of the second luminal structure is approximated with the free end of the first luminal structure by sliding the tissue connecting device longitudinally over the first elongate body distally toward the tissue approximation head.

10. The method of claim 1, wherein the tissue connection device contains a fastener selected from the group consisting of staples, clips, screws, adhesives, sutures and combinations thereof

\* \* \* \* \*